US006673834B2

United States Patent
Kurz et al.

(10) Patent No.: US 6,673,834 B2
(45) Date of Patent: Jan. 6, 2004

(54) HYDROPERYLENE DERIVATIVES

(75) Inventors: Michael Kurz, Hofheim (DE); Matthias Herrmann, Hofheim-Diedenbergen (DE); Luigi Toti, Hochheim (DE); Laszlo Vertesy, Eppstein-Vockenhausen (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 10/300,963

(22) Filed: Nov. 21, 2002

(65) Prior Publication Data

US 2003/0144349 A1 Jul. 31, 2003

Related U.S. Application Data

(60) Provisional application No. 60/360,329, filed on Feb. 27, 2002.

(30) Foreign Application Priority Data

Nov. 28, 2001 (DE) .......................................... 101 58 402

(51) Int. Cl.$^7$ .................... A61K 31/336; C07D 303/06; C07D 303/10; C07D 303/17; C07D 303/31
(52) U.S. Cl. ....................................... 514/475; 549/543
(58) Field of Search ............................ 514/475; 549/543

(56) References Cited

PUBLICATIONS

Arnone Alberto et al., Secondary Mould Metabolites. Part 16. Stemphyltoxins, New Reduced Perylenequinone Metabolites from Stemphylium botryosum var. Lactucum, J. Chem. Soc. Perkin Trans. 1, 1986, pp. 525–530.
Born G. V. R., Aggregation of Blood Platelets by Adenosine Diphosphate and its Reversal, Nature, 1962, vol. 194, pp. 927–929.
Holló Zsolt et al., Calcein accumulation as a fluorometric functional assay of the multidrug transporter, Biochim. Biophys. Acta, 1994, 1191(2), 384–388.
Okuno Toshikatsu et al., Structure of Antifungal and Phytotoxic Pigments Produced by Alternaria SPS., Tetrahedron Lett., 1983, vol. 24, 5653–5656.
Robeson D. et al., Alteichin: an unusual phytotoxin from Alternaria eichorniae, a fungal pathogen of water hyacinth, Experentia, 1984, vol. 40, 1248–1250.
Schrader T.J. et al., Examination of Alternaria alternata Mutagenicity and Effects of Nitrosylation Using the Ames Salmonella Test, Teratogenesis Carcinogenesis, and Mutagenesis, 2001, vol. 21, pp. 261–274.
Stack Michael E. et al., Mutagenic Perylenequinone Metabolites of Alternaria Alternata: Altertoxins I, II, and III, Journal of Natural Products, 1986, vol. 49, No. 5, pp. 866–887.
Stierle Andrea C. et al., Phytotoxins from Alternaria Alternata, a Pathogen of Spotted Knapweed, J. Nat. Prod, 1989, vol. 52, No. 1, 42–27.
Togashi Ken–ichi et al., Inhibition of Human Telomerase Activity by Alterperylenol, Oncology Research, 1998, vol. 10, pp. 449–453.
Remington's Pharmaceutical Sciences; 1985; (17. Chapter 76, p. 1418).
Krohn Karsten et al., Biologically Active Metabolites From Fungi 13 Stemphytriol, A New Perylene Derivative From Monodictys Fluctuata, Natural Product Letters, 1999, vol. 14(1), pp 31–34.

*Primary Examiner*—Ba K. Trinh
(74) *Attorney, Agent, or Firm*—Irving Newman

(57) ABSTRACT

Compounds of the formula I

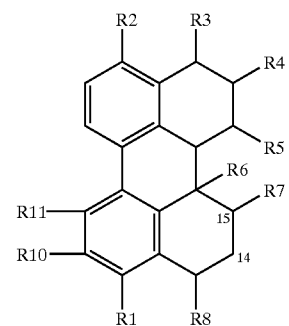

are suitable for producing pharmaceuticals for the prophylaxis and therapy of diseases in which high blood platelet aggregations occur.

9 Claims, No Drawings

HYDROPERYLENE DERIVATIVES

CROSS-REFERENCE TO RELATED APPLICATIONS

This application claims priority from Provisional U.S. Application No. 60/360,329, filed Feb. 27, 2002, as well as from Federal Republic of Germany Patent Application No. 10158402.4, filed Nov. 28, 2001.

SUMMARY OF THE INVENTION

The invention relates to hydroperylene derivatives which are formed by the fungus, DSM 14452, during fermentation, or are subsequently derivatized, to processes for preparing them and to their use as pharmaceuticals and inhibitors of blood platelets, as well as to sid novel fungus itself.

BACKGROUND OF THE INVENTION

Hydroperylene derivatives, such as hexahydroperylene derivatives or octahydroperylene derivatives, are formed by various microorganisms. Examples of known hydroperylene derivatives are:

Altertoxins I, II and III (M. E. Stark et al. J. Nat. Prod. 49, 866–871, 1986),

Alteichin (D. Robeson et al. Experientia, 40, 1248–1250, 1984), the Alterlosins (A. Stierle et al. J. Nat. Prod. 52, 42–47, 1989) and Alterperylenol from Alternaria species (T. Okuno et al. Tetrahedron Lett. 24, 5653–5656, 1983);

Stemphyltoxins and Stemphypyrenol, which are from cultures of Stemphylium botryosum (A. Arnone et al. J. Chem. Soc. Perkin Trans.1, 1986, 525–530).

The altertoxins and the stemphyltoxins are phytotoxins, which, as a result of their mutagenic effect, can also diminish the value of human foodstuffs. They have herefore been thoroughly described in more than 70 publications (T. J. Schrader et al. Teratog. Carcinog., Mutagen., 21, 261–274, 2001). The dangers which emanate from the altertoxins and stemphyltoxins are naturally dealt with in this literature, including the wide distribution, and the cancer-causing effect, of these compounds, which contain epoxides (oxiranes). In addition to this, alterperylenol has been reported to have a weak telomerase-inhibiting effect (K-I. Togashi et al. Oncol. Res. 10, 449–453, 1998); however, at 30 µM, the $IC_{50}$ value, which is characteristic for inhibition of the enzyme, is low.

Thromboembolic diseases are the most frequent cause of death, particularly in the western industrial nations. An effective prophylaxis and therapy for these diseases is therefore of exceptional importance. A thrombus is understood as being a blood clot which has been formed intravitally and intravascularly. Thrombi are formed following thrombocyte aggregation in arteries, in particular. Damage to the blood vessel wall, retarded blood flow and accelerated clotting all favor thrombus formation. The thrombocytes (blood platelets) are disc-shaped, anucleate blood cells which ensure hemostasis and blood coagulation when injury occurs. Thrombocytes bring about hemostasis by means of aggregation in a complicated process; thrombocyte aggregation is consequently an essential process for homeotherms. Hypofunction of the thrombocytes leads to severe hemorrhages, even in the case of relatively small injuries; on the other hand, an increased tendency towards coagulation increases the danger of thrombosis and embolism. Since platelet hyperfunction, in particular, frequently has fatal consequences, several substances have already been employed as inhibitors of thrombocyte aggregation. Those which are well known include acetylsalicylic acid (Aspirin®), ticlopidine (Tiklyd®) and the related clopidogrel; however, because of side-effects, the use of all these preparations is restricted. For this reason, there is a great need for inhibitors of intracellular platelet activation, which can be used for the therapy and long-term prophylaxis of arterial thromboembolic events. Agents of this nature can be employed, for example, in connection with myocardial infarction, in connection with unstable angina or in connection with strokes.

DETAILED DESCRIPTION OF THE INVENTION

In the endeavor to find effective compounds for preventing or treating blood coagulation diseases, it has now been found that thioperylenol, which is formed by the fungal strain DSM 14452, and other hydroperylene derivatives, are able to effectively inhibit blood platelet aggregation.

The invention, therefore, relates to a compound of formula I

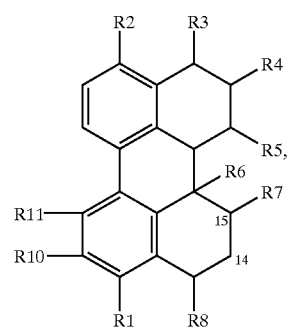

including all stereoisomeric forms of said compound of formula I, mixtures of said forms and compounds in any ratio, and physiologically tolerated salts thereof, wherein:

R1, R2, R3, R4, R5, R6, R7, R8, R10 and R11 are independently selected from the group consisting of hydrogen;

($C_1$–$C_6$)-alkyl, in which alkyl is a straight or branched chain and is unsubstituted or substituted by one, two or three substituents independently selected from the group consisting of:

—OH; =O; —O—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkenyl, in which alkenyl is a straight or branched chain and is unsubstituted or substituted by one, two or three substituents independently selected from the group consisting of:

—CN; —$NH_2$; =N—OH and =N—O—($C_1$–$C_6$)-alkyl, in which alkyl is a straight or branched chain; —O—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; -aryl, in which aryl is unsubstituted or substituted by one, two or three substituents independently selected from the group consisting of: halogen; —($C_1$–$C_4$)-alkyl, in which alkyl is a straight or branched chain; —O—($C_1$–$C_6$)-alkyl, in which alkyl is a straight or branched chain; —OH and —($C_1$–$C_4$)-alkyl, in which alkyl is a straight or branched chain and is substituted by one, two or three substituents selected from the group consisting of halogen; —C(O)—OH; —C(O)—O—$NH_2$; —C(O)—O—($C_1$–$C_4$)-alkyl, in which alkyl is a straight or branched chain; —NH—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —$NH_2$ and halogen;

($C_2$–$C_6$)-alkenyl, in which alkenyl is a straight or branched chain and is unsubstituted or substituted by one, two or three substituents independently selected from the group consisting of:
—OH; =O; —O—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; -aryl, in which aryl is unsubstituted or substituted by one, two or three substituents independently selected from the group consisting of: halogen; —($C_1$–$C_4$)-alkyl, in which alkyl is a straight or branched chain; —O—($C_1$–$C_6$)-alkyl, in which alkyl is a straight or branched chain; —OH and —($C_1$–$C_4$)-alkyl, in which alkyl is a straight or branched chain and is substituted one, two or three times by halogen; —C(O)—OH; —C(O)—O—$NH_2$; —C(O)—O—($C_1$–$C_4$)-alkyl, in which alkyl is a straight or branched chain; —NH—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —$NH_2$ and halogen;
—O—$R^9$, in which $R^9$ is selected from the group consisting of: ($C_1$–$C_6$)-alkyl, in which alkyl is a straight or branched chain and is unsubstituted or substituted by one, two or three substituents independently selected from the group consisting of: —OH; =O; —O—($C_1$-$C_6$)-alkyl, in which alkyl is a straight or branched chain and is unsubstituted or substituted by one, two or three substituents independently selected from the group consisting of: —CN; —$NH_2$; =N—OH; and =N—O—($C_1$-$C_6$)-alkyl, in which alkyl is a straight or branched chain; —O—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; -aryl, in which aryl is unsubstituted or substituted by one, two or three substituents independently selected from the group consisting of: halogen; —($C_1$-$C_4$)-alkyl, in which alkyl is a straight or branched chain; —O—($C_1$-$C_6$)-alkyl, in which alkyl is a straight or branched chain; —OH and —($C_1$-$C_4$)-alkyl, in which alkyl is a straight or branched chain and is substituted one, two or three times by halogen; —C(O)—OH; —C(O)—O—$NH_2$; —C(O)—O—($C_1$-$C_4$)-alkyl, in which alkyl is a straight or branched chain; —NH—($C_1$-$C_6$)-alkyl, in which alkyl is a straight or branched chain and is unsubstituted or substituted by one, two or three substituents independently selected from the group consisting of: —CN; —$NH_2$; =N—OH; and =N—O—($C_1$-$C_6$)-alkyl, in which alkyl is a straight or branched chain; —NH—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —NH—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —$NH_2$ and halogen;

($C_2$-$C_6$)-alkenyl, in which alkenyl is a straight or branched chain and is unsubstituted or substituted by one, two or three substituents independently selected from the group consisting of: —OH; =O; —O—($C_1$-$C_6$)-alkyl, in which alkyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkynyl, in which alkynyl is a straight or branched chain and is unsubstituted or substituted by one, two or three substituents independently selected from the group consisting of: —CN; —$NH_2$, =N—OH and =N—O—($C_1$-$C_6$)-alkyl, in which alkyl is a straight or branched chain; -aryl, in which aryl is unsubstituted or substituted by one, two or three substituents independently selected from the group consisting of: halogen; —($C_1$-$C_4$)-alkyl, in which alkyl is a straight or branched chain; —O—($C_1$-$C_6$)-alkyl, in which alkyl is a straight or branched chain; —OH and —($C_1$-$C_4$)- alkyl, in which alkyl is a straight or branched chain and is substituted one, two or three times by halogen; —C(O)—OH; —C(O)—O—NH$_2$; —C(O)—O—(C$_1$–C$_4$)-alkyl, in which alkyl is a straight or branched chain; —NH—(C$_1$–C$_6$)-alkyl, in which alkyl is a straight or branched chain and is unsubstituted or substituted by one, two or three substituents independently selected from the group consisting of: —CN; —NH$_2$; =N—OH; and =N—O—(C$_1$–C$_6$)-alkyl, in which alkyl is a straight or branched chain; —NH—(C$_2$–C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH—(C$_2$–C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH$_2$ and halogen;
—NH—R$^9$, in which R$^9$ is as defined above;
—NH—C(O)—H;
—NH—C(O)—R$^9$, in which R$^9$ is as defined above;
—NH-aryl, in which aryl is unsubstituted or independently substituted one, two or three times by R$^9$, in which R$^9$ is as defined above:
=N—OH;
=N—O—R$^9$, in which R$^9$ is as defined above;
—S—H;
—S—R$^9$, in which R$^9$ is as defined above;
—S(O)—R$^9$, in which R$^9$ is as defined above;
—S(O)$_2$—R$^9$, in which R$^9$ is as defined above; and
—SO$_2$, with the following further alternatives to the foregoing definition:
a) either R4 and R5 or R10 and R11, together with the carbon atoms to which they are, respectively, bonded, may form a 3-, 4-, 5- or 6-membered heteroalkyl or heteroaryl ring system which contains one or two heteroatoms selected from the group consisting of oxygen, nitrogen and sulfur; and
b) the bond between the ring carbons indicated as —C$_{14}$–C$_{15}$— in formula I may be either a single bond or a double bond; and the further proviso that:
c) R7 is not hydrogen.

The invention also relates to a compound of formula I, wherein
each of R1, R2, R3 and R6 is —OH;
R4 and R5, together with the carbon atom to which they are bonded, form an epoxide;
R7 is the radical —S—CH$_2$—CHOH—COOH;
R8 is =O;
R10 and R11 are each hydrogen;
and the bond between —C$_{14}$–C$_{15}$— is a single bond.

The invention also relates to optically pure compounds of the formula I and to their stereoisomeric mixtures, such as enantiomeric mixtures and diasteromeric mixtures, in any ratio to each other.

The term "halogen" is understood as meaning fluorine, chlorine, bromine or iodine. The term "(C$_1$–C$_6$)-alkyl" is understood as meaning hydrocarbon radicals whose carbon chain is straight-chain or branched and contains from 1 to 6 carbon atoms, for example methyl, ethyl, propyl, i-propyl, butyl, tertiary butyl, pentyl and hexyl. The term "(C$_2$–C$_6$)-alkenyl" is understood as meaning hydrocarbon radicals whose carbon chain is straight-chain or branched and contains from 2 to 6 carbon atoms, and which exhibits one, two or three double bonds, for example the radicals allyl, crotyl, 1-propenyl, penta-1,3-dienyl, pentenyl and hexenyl. The term "(C$_2$–C$_6$)-alkynyl" is understood as meaning hydrocarbon radicals whose carbon chain is straight-chain or branched and contains from 2 to 6 carbon atoms and which exhibits one or two triple bonds, for example the radicals propynyl, butynyl and pentynyl. The term "aryl" is understood as meaning the radicals phenyl, benzyl, 1-naphthyl and 2-naphthyl. The expression "R4 and R5, together with the carbon atoms to which they are in each case bonded, form a 3-, 4-, 5- or 6-membered ring system which is aromatic or saturated and which contains one or two heteroatoms from the series oxygen, nitrogen or sulfur" is understood as meaning radicals such as epoxide, aziridine, azetidine, azetine, pyrrole, pyrrolidine, pyridine, piperidine, tetrahydropyridine, pyrazole, imidazole, pyrazoline, imidazoline, pyrazolidine, imidazolidine, pyridazine, pyrimidine, pyrazine, piperazine, pyran, oxazole, isoxazole, 2-isoxazoline, isoxazolidine, morpholine, oxothiolane, thiopyran, thiazole, isothiazole, 2-isothiazoline, isothiazolidine or thiomorpholine.

The invention furthermore relates to the compound of the formula II

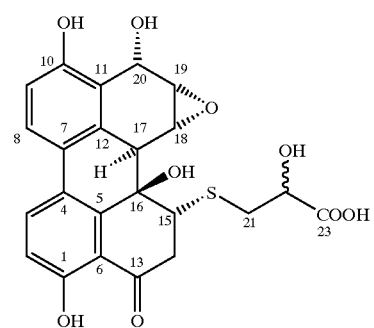

II

In the description which follows, the compound of the formula II is termed thioperylenol (empirical formula: C$_{23}$H$_{20}$NO$_9$S; molecular weight 472.47) and to the physiologically tolerated salts thereof.

The invention furthermore relates to a process for preparing a compound of formula I, and/or a stereoisomeric form of a compound of the formula I and/or mixtures of these forms in any ratio, and/or a physiologically tolerated salt of a compound of formula I, which process comprises
a) culturing the microorganism DSM 14452, or its mutants or variants, in an aqueous nutrient medium and isolating and purifying the compound thioperylenol, or
b) converting thioperylenol, by means of chemical derivatization, into a compound of the formula I, or
c) resolving a compound of the formula I, which has been prepared by methods a) or b) and which, because of its chemical structure, appears in enantiomeric forms, into the pure enantiomers by forming salts with enantiomerically pure acids or bases, by chromatography on chiral stationary phases or by derivatizing with chiral, enantiomerically pure compounds such as amino acids, separating the diastereomers which are thus obtained and eliminating the chiral auxiliary groups, or
d) either isolating the compound of the formula I which has been prepared by the methods a), b) or c) in free form or, when acidic or basic groups are present, converting it into physiologically tolerated salts.

The microorganism DSM 14452 (internal designation ST003367) belongs to the fungal group and possesses a white substrate mycelium and very little aerial mycelium and was deposited on Aug. 3, 2001, under the conditions of the Budapest Treaty, in the DSMZ-Deutsche Sammlung von Mikroorganismen und Zellkulturen [German collection of microorganisms and cell cultures] GmbH, Mascheroder Weg 1b, D-38124 Braunschweig, under the number DSM 14452.

Variants of DSM 14452 are understood as being DSM 14452 strains which have been obtained by isolating individual colonies from a culture of DSM 14452 on the proviso that they produce thioperylenol. Mutants of DSM 14452 are understood as being DSM 14452 strains which have been obtained from a culture of DSM 14452 after mutation, with the proviso that they produce thioperylenol. Mutants of DSM 14452 can be generated, in a manner known per se, by physical means, for example irradiation, such as ultraviolet or X-ray radiation, or by using chemical mutagens, for example ethyl methanesulfonate (EMS); 2-hydroxy-4-methoxybenzophenone (MOB) or N-methyl-N'-nitro-N-nitrosoguanidine (MNNG).

The mutants are found, for example, by taking samples from the culture medium and determining the inhibitory effect of thioperylenol.

Thioperylenol is produced by culturing DSM 14452. The nutrient solution contains carbon sources, such as sucrose, corn starch, dextrose, lactose, D-mannitol, molasses or malt extract, and nitrogen sources, such as soybean flour, peanut flour, proteins, peptones, peptides, tryptones, meat extract, yeast extract or ammonium salts or nitrates.

The nutrient solution also contains inorganic salts such as sodium hydrogen phosphate, sodium chloride, calcium chloride, calcium sulfate, calcium carbonate, magnesium sulfate or potassium hydrogen phosphate. In addition, it is also possible to add fat, such as methyl oleate or soybean oil, to the nutrient medium. Besides that, trace elements, such as iron salts, manganese salts, copper salts, zinc salts or cobalt salts, or other metal salts, are also added.

A preferred nutrient solution contains from about 0.05% to about 5%, preferably from about 1% to about 3%, potato dextrose and from about 0.05% to about 3%, preferably from about 0.05% to about 1%, yeast extract. The percentages relate to the weight of the total nutrient solution.

DSM 14452 is cultured at temperatures of from about 18° C. to about 35° C., preferably at from about 23° C. to about 28° C., and at pH values of from about 3 to about 10, preferably from about 5 to about 9, particularly preferably at values of from about 4 to about 6. The culture is carried out aerobically, initially in shaking flasks and, after that, in a fermenter while stirring and aerating with air or pure oxygen. The microorganisms are cultured in the fermenters for a period of from about 48 to about 720 hours, preferably of from about 72 to about 144 hours.

The formation of thioperylenol reaches its maximum after from about 96 to about 144 hours.

The fungal strain DSM 14452 also forms mixtures of several compounds of formula I in the nutrient solution. The quantitative proportion of the compounds of formula I in the mixture can vary depending on the composition of the nutrient solution. In addition, the composition of the medium can be used to direct the synthesis of individual compounds of formula I such that the microorganism either does not produce individual compounds of formula I at all or only produces them in a quantity which is below the limit of detection.

Thioperylenol is either isolated directly from the nutrient solution or isolated after the cells have been separated off, for example by means of centrifugation or filtration. The thioperylenol can be isolated by extracting with solvents or by adsorbing on resins such as XAD 16, HP 20, MCI Gel® CHP20P or ion exchangers. It is purified, for example, by chromatography on adsorption resins such as on Diaion® HP-20 (Mitsubishi Casei Corp., Tokyo), on Amberlite® XAD 7 (Rohm and Haas, USA), or on Amberchrom® CG (Toso Haas, Philadelphia, USA). The separations can be carried out over a wide pH range. The range of pH 1 to pH 9 is preferred, with the range of pH 2 to pH 8 being particularly preferred. In addition to this, reverse phase supports, which are used within the context of high pressure liquid chromatography (HPLC), are also suitable. Another isolation method is that of using molecular sieves such as Fractogel® TSK HW-40S or Sephadex® LH-20.

The microbiologically produced thioperylenol is used as the starting material for preparing the thioperylenol derivative. The compounds of formula I are prepared in a manner known per se; for example, the epoxide group of the thioperylene can be converted by hydrolysis or solvolysis into alcohols or esters. Epoxides are very reactive compounds which, in addition to water and acids, also add on other nucleophilic reagents, such as alcohols, thiols, amines and Grignard compounds, in the presence of acidic or basic catalysts. The addition of hydrogen cyanide leads further on to β-hydroxy-propionitrile derivatives. In addition to this, epoxides can be rearranged to give carbonyl-derivatives, with this rearrangement being catalyzed, for example, by Lewis acids. In addition, the reaction products can be subjected to further reactions. These reactions are known per se and are described, for example, by Jerry March, Advanced Organic Chemistry, John Wiley & Sons, $4^{th}$ Edition, 1992.

Other derivatives are obtained if the 3-thio-lactic acid radical of the thioperylenol is reacted reductively or oxidatively. It can also be advantageous to use the sulfide as what is termed a leaving group and replace it with other suitable radicals in a manner known from the literature. In order to carry out reactions selectively, it can be advantageous to introduce suitable protecting groups, in a manner known per se, prior to the reaction. The protecting groups are eliminated after the reaction and the reaction product is then purified.

Pharmacologically tolerated salts of compounds of formula I are understood as being both inorganic and organic salts, as are described in Remington's Pharmaceutical Sciences (17th edition, page 1418 (1985)). Physiologically tolerated salts are prepared in a manner known per se from compounds of formula I, including their stereoisomeric forms, which are capable of forming salts. With basic reagents, such as hydroxides, carbonates, hydrogen carbonates, alcoholates and ammonia, or organic bases, for example, trimethylamine, triethylamine, ethanolamine or triethanolamine, or else basic amino acids, for example, lysine, ornithine or arginine, the carboxylic acid forms stable alkali metal salts, alkaline earth metal salts or, where appropriate, substituted ammonium salts. If a compound of formula I possesses basic groups, it is also possible to prepare stable acid addition salts with strong acids. Both inorganic acids and organic acids, such as hydrochloric acid, hydrobromic acid, sulfuric acid, benzenesulfonic acid, phosphoric acid, methanesulfonic acid, p-toluenesulfonic acid, 4-bromobenzenesulfonic acid, trifluoromethylsulfonic acid, cyclohexylamidosulfonic acid, acetic acid, oxalic acid, tartaric acid, succinic acid and trifluoroacetic acid, are suitable for this purpose.

The invention also relates to pharmaceuticals which are characterized by an effective content of at least one compound of the formula I and/or a physiologically tolerated salt of the compound of the formula I and/or an optionally stereoisomeric form of the compound of the formula I, together with a pharmaceutically suitable and physiologically tolerated carrier substance, additive and/or other active compounds and auxiliary substances.

On account of their pharmacological properties, the compounds of formula I are suitable for the prophylaxis and therapy of all those diseases in which high blood platelet aggregations occur and which are caused by thrombus formation or embolisms. These diseases include, for example, myocardial infarction, unstable angina pectoris, stroke, transitory ischemic attacks and peripheral arterial occlusion diseases (peripheral vascular disease) such as intermittent claudication.

The invention also relates to the use of at least one compound of formula I and/or all stereoisomeric forms of the compounds of formula I and/or mixtures of these forms in any ratio, and/or a physiologically tolerated salt of the compound of the formula I, for producing pharmaceuticals for the prophylaxis and therapy of diseases in which high blood platelet aggregations occur, where R1, R2, R3, R4, R5, R6, R7, R8, R10 and R11 R1, R2, R3, R4, R5, R6, R7, R8, R10 and R11 are independently selected from the group consisting of hydrogen;

($C_1$–$C_6$)-alkyl, in which alkyl is a straight or branched chain and is unsubstituted or substituted by one, two or three substituents independently selected from the group consisting of:

—OH; =O; —O—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; -aryl, in which aryl is unsubstituted or substituted by one, two or three substituents independently selected from the group consisting of: halogen; —($C_1$–$C_4$)-alkyl, in which alkyl is a straight or branched chain; —O—($C_1$–$C_6$)-alkyl, in which alkyl is a straight or branched chain; —OH and —($C_1$–$C_4$)-alkyl, in which alkyl is a straight or branched chain and is substituted by one, two or three substituents selected from the group consisting of halogen; —C(O)—OH; —C(O)—O—$NH_2$; —C(O)—O—($C_1$–$C_4$)-alkyl, in which alkyl is a straight or branched chain; —NH—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —$NH_2$ and halogen;

($C_2$–$C_6$)-alkenyl, in which alkenyl is a straight or branched chain and is unsubstituted or substituted by one, two or three substituents independently selected from the group consisting of:

—OH; =O; —O—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkenyl, in which alkenyl is a straighten branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; -aryl, in which aryl is unsubstituted or substituted by one, two or three substituents independently selected from the group consisting of: halogen; —($C_1$–$C_4$)-alkyl, in which alkyl is a straight or branched chain; —O—($C_1$–$C_6$)-alkyl, in which alkyl is a straight or branched chain; —OH and —($C_1$–$C_4$)-alkyl, in which alkyl is a straight or branched chain and is substituted one, two or three times by halogen; —C(O)—OH; —C(O)—O—$NH_2$; —C(O)—O—($C_1$–$C_4$)-alkyl, in which alkyl is a straight or branched chain; —NH—($C_1$–$C_6$)-alkyl, in which alkyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —$NH_2$ and halogen;

($C_2$–$C_6$)-alkynyl, in which alkynyl is a straight or branched chain and is unsubstituted or substituted by one, two or three substituents independently selected from the group consisting of:

—OH; =O; —O—(C$_1$–C$_6$)-alkyl, in which alkyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —O—(C$_2$–C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —O—(C$_2$–C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; -aryl, in which aryl is unsubstituted or substituted by one, two or three substituents independently selected from the group consisting of: halogen; —(C$_1$–C$_4$)-alkyl, in which alkyl is a straight or branched chain; —O—(C$_1$–C$_6$)-alkyl, in which alkyl is a straight or branched chain; —OH and —(C$_1$–C$_4$)-alkyl, in which alkyl is a straight or branched chain and is substituted one, two or three times by halogen; —C(O)—OH; —C(O)—O—NH$_2$; —C(O)—O—(C$_1$–C$_4$)-alkyl, in which alkyl is a straight or branched chain; —NH—(C$_1$–C$_6$)-alkyl, in which alkyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH—(C$_2$–C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH—(C$_2$–C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH$_2$ and halogen;

—O—R$^9$, in which R$^9$ is selected from the group consisting of: (C$_1$–C$_6$)-alkyl, in which alkyl is a straight or branched chain and is unsubstituted or substituted by one, two or three substituents independently selected from the group consisting of: —OH; =O; —O—(C$_1$–C$_6$)-alkyl, in which alkyl is a straight or branched chain and is unsubstituted or substituted by one, two or three substituents independently selected from the group consisting of: —CN; —NH$_2$; =N—OH; and =N—O—(C$_1$–C$_6$)-alkyl, in which alkyl is a straight or branched chain; —O—(C$_2$–C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —O—(C$_2$–C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; -aryl, in which aryl is unsubstituted or substituted by one, two or three substituents independently selected from the group consisting of: halogen; —(C$_1$–C$_4$)-alkyl, in which alkyl is a straight or branched chain; —O—(C$_1$–C$_6$)-alkyl, in which alkyl is a straight or branched chain; —OH and —(C$_1$–C$_4$)-alkyl, in which alkyl is a straight or branched chain and is substituted one, two or three times by halogen; —C(O)—OH; —C(O)—O—NH$_2$; —C(O)—O—(C$_1$–C$_4$)-alkyl, in which alkyl is a straight or branched chain; —NH—(C$_1$–C$_6$)-alkyl, in which alkyl is a straight or branched chain and is unsubstituted or substituted by one, two or three substituents independently selected from the group consisting of: —CN; —NH$_2$; =N—OH; and =N—O—(C$_1$–C$_6$)-alkyl, in which alkyl is a straight or branched chain; —NH—(C$_2$–C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH—(C$_2$–C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH$_2$ and halogen;

(C$_2$–C$_6$)-alkenyl, in which alkenyl is a straight or branched chain and is unsubstituted or substituted by one, two or three substituents independently selected from the group consisting of: —OH; =O; —O—(C$_1$–C$_6$)-alkyl, in which alkyl is a straight or branched chain and is unsubstituted or substituted by one, two or three substituents independently selected from the group consisting of: —CN; —NH$_2$; =N—OH; and =N—O—(C$_1$–C$_6$)-alkyl, in which alkyl is a straight or branched chain; —O—(C$_2$–C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —O—(C$_2$–C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; -aryl, in which aryl is unsubstituted or substituted by one, two or three substituents independently selected from the group consisting of: halogen; —(C$_1$–C$_4$)-alkyl, in which alkyl is a straight or branched chain; —O—(C$_1$–C$_6$)-alkyl, in which alkyl is a straight or branched chain; —OH and —(C$_1$–C$_4$)-alkyl, in which alkyl is a straight or branched chain and is substituted one, two or three times by halogen; —C(O)—OH; —C(O)—O—NH$_2$; —C(O)—O—(C$_1$-C$_4$)-alkyl, in which alkyl is a straight or branched chain; —NH—(C$_1$-C$_6$)-alkyl, in which alkyl is a straight or branched chain and is unsubstituted or substituted by one, two or three substituents independently selected from the group consisting of: —CN; —NH$_2$; =N—OH; and =N—O—(C$_1$-C$_6$)-alkyl, in which alkyl is a straight or branched chain; —NH—(C$_2$-C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$-C$_6$)-alkyl, in which alkyl is a straight or branched chain; —NH—(C$_2$-C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$-C$_6$)-alkyl, in which alkyl is a straight or branched chain; —NH$_2$ and halogen; (C$_2$-C$_6$)-alkynyl, in which alkynyl is a straight or branched chain and is unsubstituted or substituted by one, two or three substituents independently selected from the group consisting of: —OH; =O; —O—(C$_1$-C$_6$)-alkyl, in which alkyl is a straight or branched chain and is unsubstituted or substituted by one, two or three substituents independently selected from the group consisting of: —CN; —NH$_2$; =N—OH; and =N—O—(C$_1$-C$_6$)-alkyl, in which alkyl is a straight or branched chain; —O—(C$_2$-C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$-C$_6$)-alkyl, in which alkyl is a straight or branched chain; —O—(C$_2$-C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$-C$_6$)-alkyl, in which alkyl is a straight or branched chain; -aryl, in which aryl is unsubstituted or substituted by one, two or three substituents independently selected from the group consisting of: halogen; —(C$_1$-C$_4$)-alkyl, in which alkyl is a straight or branched chain; —O—(C$_1$-C$_6$)-alkyl, in which alkyl is a straight or branched chain; —OH and —(C$_1$-C$_4$)-alkyl, in which alkyl is a straight or branched chain and is substituted one, two or three times by halogen; —C(O)—OH; —C(O)—O—NH$_2$; —C(O)—O—(C$_1$-C$_4$)-alkyl, in which alkyl is a straight or branched chain; —NH—(C$_1$-C$_6$)-alkyl, in which alkyl is a straight or branched chain and is unsubstituted or substituted by one, two or three substituents independently selected from the group consisting of: —CN; —NH$_2$; =N—OH; and =N—O—(C$_1$-C$_6$)-alkyl, in which alkyl is a straight or branched chain; —NH—(C$_2$-C$_6$)-alkenyl, in which alkenyl is a straight or branched chain and is unsubstituted or substituted by one, two or three substituents independently selected from the group consisting of: —CN; —NH$_2$; =N—OH and =N—O—(C$_1$-C$_6$)-alkyl, in which alkyl is a straight or branched chain; —NH—(C$_2$-C$_6$)-alkynyl, in which alkynyl is a straight or branched chain and is unsubstituted or substituted by one, two or three substituents independently selected from the group consisting of: —CN; —NH$_2$; =N—OH and =N—O—(C$_1$-C$_6$)-alkyl, in which alkyl is a straight or branched chain; —NH$_2$ and halogen;

—NH—R$^9$, in which R$^9$ is as defined above;
—NH—C(O)—H;
—NH—C(O)—R$^9$, in which R$^9$ is as defined above;
—NH-aryl, in which aryl is unsubstituted or independently substituted one, two or three times by R$^9$, in which R$^9$ is as defined above:
=N—OH;
=N—O—R$^9$, in which R$^9$ is as defined above;
—S—H;
—S—R$^9$, in which R$^9$ is as defined above;
—S(O)—R$^9$, in which R$^9$ is as defined above;
—S(O)$_2$—R$^9$, in which R$^9$ is as defined above; and
—SO$_2$, with the following further alternatives to the foregoing definition:

a) either R4 and R5 or R10 and R11, together with the carbon atoms to which they are, respectively, bonded, may form a 3-, 4-, 5- or 6-membered heteroalkyl or heteroaryl ring system which contains one or two heteroatoms selected from the group consisting of oxygen, nitrogen and sulfur; and b) the bond between the ring carbons indicated as —C$_{14}$-C$_{15}$— in formula I may be either a single bond or a double bond; and the further proviso that:

c) R7 is not hydrogen.

The invention also relates to a process for producing a pharmaceutical, which process comprises bringing at least one compound of the formula I, together with a pharmaceutically suitable and physiologically tolerated excipient and, where appropriate, other suitable active compounds, additives or auxiliary substances, into a suitable form for administration.

Examples of suitable solid or galenic preparation forms are granules, powders, sugar-coated tablets, tablets, (micro) capsules, suppositories, syrups, juices, suspensions, emulsions, drops or injectable solutions and preparations having a protracted release of the active compound, in the production of which use is made of customary adjuvants such as carrier substances, disintegrants, binders, coating agents, swelling agents, glidants or lubricants, flavorings, sweeteners and solubilizers. Frequently employed auxiliary substances which may be mentioned are: magnesium carbonate, titanium dioxide, lactose, mannitol and other sugars, talc, milk protein, gelatin, starch, cellulose and its derivatives, animal and vegetable oils, such as cod liver oil, sunflower oil, peanut oil or sesame oil, polyethylene glycol and solvents, such as sterile water and monohydric or polyhydric alcohols, such as glycerol.

The pharmaceutical preparations are preferably produced and administered in dosage units, with each unit containing, as the active constituent, a particular dose of the compound of the formula I according to the invention. In the case of solid dosage units, such as tablets, capsules, sugar-coated tablets or suppositories, this dose can be from 0.1 mg/kg of body weight to 1,000 mg/kg of body weight, preferably from 0.2 mg/kg of body weight to 100 mg/kg of body weight. They are expediently administered in dosage units which contain at least the effective daily quantity of the compound of the formula I, for example up to 1000 mg, preferably, however, from about 50 to 300 mg and, in the case of injection solutions in ampule form, up to about 300 mg, preferably, however, from about 10 to 100 mg.

Daily doses of from about 20 mg to 1,000 mg, preferably from about 100 mg to 500 mg, of active compound, depending on the activity of the compound according to formula I, are indicated for treating an adult patient of about 70 kg in weight. However, it may possibly also be appropriate to use higher or lower daily doses. The daily dose can be administered either by means of a once-only administration in the form of a single dosage unit or of several smaller dosage units or by means of a repeated administration of subdivided doses at particular intervals.

The microorganism DSM 14452 is also part of the subject matter of the invention.

The following examples are intended to illustrate the invention without thereby restricting the scope of the invention in any way.

EXAMPLE 1

Preparing a Glycerol Culture of the Fungal Strain DSM 14452

30 ml of nutrient solution (malt extract, 2.0%, yeast extract, 0.2%, glucose, 1.0%, $(NH_4)_2HPO_4$, 0.05%, pH 6.0) in a sterile 100 ml Erlenmeyer flask were inoculated with the fungal strain ST 003367, DSM 14452, and incubated at 25° C. and 140 revolutions per minute (rpm) on a rotating shaker for 6 days. 1.5 ml of this culture were subsequently diluted with 2.5 ml of 80% glycerol and stored at −135° C.

EXAMPLE 2

Preparing a Preliminary Culture of the Fungus DSM 14452 (in an Erlenmeyer Flask)

100 ml of nutrient solution (malt extract, 2.0%, yeast extract, 0.2%, glucose, 1.0%, $(NH_4)_2HPO_4$, 0.05%, pH 6) in a sterile 300 ml Erlenmeyer flask were inoculated with the fungal strain ST 003367, DSM 14452, and incubated at 25° C. and 140 rpm on a rotating shaker for 4 days. 2 ml of this preliminary culture were subsequently required for preparing the main cultures.

EXAMPLE 3

Preparing Thioperylenol by Culturing the Fungal Strain DSM 14452

In the flask:

A sterile 300 ml Erlenmeyer flask containing 100 ml of the following nutrient solution: potato dextrose, 2.4%, yeast extract, 0.2%, pH 5.1, was inoculated with a culture which had been grown on a sloping tube (same nutrient solution but containing 2% agar), or with 2 ml of a preliminary culture, as described in example 2, and incubated at 25° C. and 140 rpm on a shaker. The maximum production of one or more compounds of the formula I was achieved after about 96 hours.

In the fermenter:

The preliminary culture of the strain ST 003367, DSM 14452, was grown at 25° C. and 140 rpm in a 2 L Erlenmeyer flask (volume in the flask, 500 mL). The fermenter was inoculated after 72 h. The strain was fermented in 8 L fermenters. The conditions for the fermentation were set as follows and led to the production of the compound according to the invention thioperylenol:

Temperature=25° C.; gassing=0.5 wm; rotational speed= 200–220 revolutions per minute (rpm); inoculum=6%; culturing time=96 hours (h).

Nutrient Media:

| Preliminary culture | |
|---|---|
| Malt extract | 20 g/L |
| Yeast extract | 2 g/L |
| Glucose | 10 g/L |
| $(NH_4)_2PO_4$ | 0.5 g/l |
| Main culture | |
| Potato dextrose broth | 24 g/L |
| Yeast extract | 2 g/L |
| Desmophene | 1.25 mL/L |

It was possible to suppress foam formation by repeatedly adding ethanolic polyol solution. The maximum production was reached after from about 96 to 144 hours.

EXAMPLE 4

Isolating the Natural Product Thioperylenol 15 liters of the culture solution obtained in accordance with example 3 were freed from the cell mass by centrifugation. The mycelium (1.5 liters) is extracted with 5 liters of methanol. The clear alcoholic phase was concentrated down to about 2 liters under reduced pressure and combined with the culture filtrate. The turbid aqueous solution was then loaded onto a 1 L-capacity column which was filled with the absorption resin MCI Gel® CHP20P. Column dimensions: width x height: 6 cm×35 cm. The column was eluted with a solvent gradient of 0.1% ammonium formate buffer, pH 4.5, in water after 2-propanol. The column effluent (60 mL/minute) was collected in fractions of in each case 220 mL. The thioperylenol-containing fractions 21 and 22, which were tested by HPLC analyses, were collected and concentrated under reduced pressure. The thioperylenol was obtained in pure form by repeated preparative HPLC on SP 250/21 NUCLEOSIL 100-7 C18 HD® columns (Macherey-Nagel, Düren) using the eluent 0.1% ammonium formate, pH 4.8, in water/95% acetonitrile in a gradient method. The flow rate through the column was 25 mL/minute and the thioperylenol was eluted from the separating column with an acetonitrile content of about 25%. 10 mg of crystalline thioperylenol were obtained by slowly concentrating under reduced pressure.

EXAMPLE 5

High-Pressure Liquid Chromatography (HPLC) of the Thioperylenol

| | |
|---|---|
| Column: | YMC-Pack Pro C18 ®, AS-303, 250 × 4.6 mm, S-5 µm; |
| Mobile Phase: | 0 to 2 minutes: 0.02% trifluoroacetic acid (TFA), 2 to 20 minutes: 0% to 100% acetonitrile in 0.1% TFA, 20 to 25 minutes: 100% acetonitrile. |
| Flow rate: | 1 mL per minute, |

Detection by UV Absorption at 210 nm.

The retention time for thioperylenol was found to be 12.1 minutes.

EXAMPLE 6

Properties of Thioperylenol

The physicochemical and spectroscopic properties of thioperylenol can be summarized as follows:

Appearance:

Brownish crystals which are soluble in medium-polar and polar organic solvents and soluble in aqueous neutral buffers. Stable in neutral and mildly acidic, non-oxidizing medium but unstable in strongly acidic and strongly alkaline solution.

| | | | |
|---|---|---|---|
| Empirical formula: | $C_{23}H_{20}O_9S$, | molecular weight: | 472.47 |
| $^1H$ and $^{13}C$ NMR: | see table 1; | | |

UV maxima in water/acetonitrile (1 to 1), pH 3.0: 216 nm, 259 nm, 292 nm and 383 nm.

TABLE 1

Chemical shifts of V-2474 in DMSO at 300K.

| Position | $^1H$ | $^{13}C$ |
|---|---|---|
| 1 | — | 160.14 |
| 2 | 7.01 | 118.22 |
| 3 | 8.05 | 132.57 |
| 4 | — | 125.12 |
| 5 | — | 137.09 |
| 6 | — | 113.86 |
| 7 | — | 122.82 |
| 8 | 7.53 | 123.75 |
| 9 | 6.79 | 113.50 |
| 10 | — | 156.37 |
| 11 | — | 122.66 |
| 12 | — | 128.08 |
| 13 | — | 204.10 |
| 14 | 3.62/3.06 | ~39.1 |
| 15 | 4.29 | 46.56 |
| 16 | — | 70.80 |
| 17 | 3.64 | 41.35 |
| 18 | 3.93 | 49.15 |
| 19 | 3.44 | 55.30 |
| 20 | 5.11 | 59.67 |
| 21 | 2.92/2.76 | 36.23 |
| 22 | 3.72 | 72.96 |
| 23 | — | 174.38 |

EXAMPLE 7

Mass Spectrometric Characterization of Thioperylenol

Thioperylenol is assigned the mass of 472 on the basis of the following findings: the ESI$^+$ spectrum gave weak peaks at 490 amu (M+NH$_4$)$^+$ and 962 amu (2M+NH$_4$)$^+$. The ESI$^-$ spectrum gave a peak, inter alia, at 471 amu (M–H)$^-$.

Using an FTICR mass spectrometer, a peak was observed, inter alia, at 569.0525 amu in the ESI$^-$ mode and in the added presence of phosphoric acid. The measured value agrees well with that calculated for (M+H$_2$PO$_4$)$^-$ = $C_{23}H_{22}O_{13}PS$=569.0524 amu (0.2 ppm difference). MS/MS experiments using an FTICR mass spectrometer led to the following fragmentations in the ESI$^-$ mode: 471 amu to 349 amu (—$C_3H_6O_3S$), 331 amu (—$C_3H_8O_4S$), 313 amu (—$C_3H_{10}O_5S$), 303 amu (—$C_4H_8O_5S$), 285 amu (—$C_4H_{10}O_6S$), 261 amu (—$C_6H_{10}O_6S$) and smaller fragments.

Pharmacological Examples

The inhibition of platelet aggregation can be measured, inter alia, by determining platelet aggregation turbimetrically as described by Born (Born, GV, Nature, 1962,194: 927–929).

Principle of the test: the method is based on the property that the optical density of a particle suspension depends on the number of particles and not on their size. After a platelet suspension has been stimulated, the platelets begin to aggregate. This leads to the appearance of relatively large platelet aggregates and to an increase in light transmission. This increase is registered photometrically, and recorded in curve form, continuously. The degrees to which the thrombocytes can be aggregated, or to which this aggregation can be inhibited, can be deduced from the changes in light transmission. The method of staining cells with calcein was used for determining cytotoxicity (Hollo Z et al., Biochim Biophys Acta 11;1191(2):384–8, 1994). Living cells incorporate the substrate calcein acetoxymethyl ester (C-AM), which is hydrolyzed in the cells by nonspecific esterases. C-AM is colorless and does not fluoresce. In the living cell, it is converted into the fluorescent hydrolysis product and the vitality of the cells can be measured on the basis of the fluorescence ($\lambda_{ex}$:485 nm/$\lambda_{em}$:538 nm).

By way of example, Table 2 summarizes the inhibitory effects of some hydroperylene derivatives as IC$_{50}$ values. The IC$_{50}$ value indicates the concentration which inhibits thrombocyte aggregation by 50% under defined conditions.

TABLE 2

The concentrations of some hydroperylene derivatives which inhibit thrombocyte aggregation by 50% (IC$_{50}$).

| Compound | IC$_{50}$ (platelet aggregation) | IC$_{50}$ (toxicity) |
|---|---|---|
| Thioperylenol | 7.2 μM | 61 μM |
| Alterperylenol | 1.6 μM | >100 μM |
| Altertoxin I | 29 μM | >100 μM |
| Altertoxin II | 2.6 μM | 10 μM |
| Altertoxin III | 6.1 μM | 20 μM |

As can be seen from the table, in addition to inhibiting thrombocyte aggregation, some of the hydroperylene derivatives also exhibit a substantial degree of cell toxicity. The cell toxicity is particularly marked in the case of compounds which carry epoxide groups. For this reason, those compounds of the formula I which, while possessing an inhibitory effect on platelet aggregation, are relatively nontoxic are particularly valuable. Preference is consequently given to hydroperylenol derivatives which are epoxide-free.

EXAMPLE 8

Test for Inhibition of Thrombocyte Aggregation

The following reagents are required for implementing the thrombocyte aggregation test:

| Materials | Supplier | Catalogue No. |
|---|---|---|
| Water tissue culture grade | Sigma | W-3500 |
| NaCl | Merck | 1.06404 |
| KCl | Merck | 1.04933 |
| CaCl$_2$ | Merck | 1.02083 |
| Albumin, bovine (BSA) | Sigma | A-6003 |
| Calcein AM | Molecular Probes | C-1430 |
| Collagen reagent | Nycomed | 5368 |
| Human alpha Thrombin | Haemochrom Diagnostica | HT1002A |

The assay was carried out as follows:

Tyrode Buffer:

| | |
|---|---|
| NaCl | 120 mM |
| KCl | 2.6 mM |
| NaHCO3 | 12 mM |
| NaH$_2$PO$_4$ × H$_2$O | 0.39 mM |
| Hepes | 10 mM |
| Glucose | 5.5 mM |
| BSA | 0.35% |

Add fresh glucose and BSA daily

Adjust pH to 7.4

Calcein AM: 1 mg of Calcein AM in 1 ml of DMSO (1 mM)

Human α-thrombin (stock solution): 1000 units in 1 ml of 0.9% NaCl

Final concentration of activator: 0.05 U of thrombin/ml or 1 μg of collagen/ml

Wortmannin, stock solution: 1 mg in 233.43 μl of DMSO (10 mM).

Aggregation in Aggregometer (PAP 4)

Cell number, 3×10$^5$ thrombocytes/μl

Mixture in siliconized glass microtubes

Total volume, 400 μl/tube

Per Microtube:

320 μl of thrombocytes

20 μl of 10 mM CaCl$_2$ (f.c. 0.5 mM)

20 μl of test substance

40 μl of agonist

Controls:

| | |
|---|---|
| Blank: | 400 μl of buffer (Tyrode, 0.35% BSA) |
| Negative control: | 320 μl of thrombocytes |
| | 40 μl of CaCl$_2$ 5 mM (f.c. 0.5 mM) |
| | 40 μl of buffer |
| Positive control: | 320 μl of buffer |
| | 40 μl of 5 mM CaCl$_2$ (f.c. 0.5 mM) |
| | 40 μl of activator |

The blank value for the channels of the aggregometer is first of all adjusted using buffer. The thrombocytes are then pipetted into microtubes and, after the thrombocytes have been added, heated at 37° C. for a few minutes in the aggregometer. After a magnetic stirrer has been added to each reaction tube, the substances, and CaCl$_2$, are added and a start is made in recording the course of the curve in the aggregometer. After 2 minutes of incubation, the activator, or buffer in the case of the control, is added. The course of the curve is then recorded for a further 6 min at 37° C. and at a stirrer speed of 1050 revolutions per minute.

What is claimed is:
1. A compound of formula I

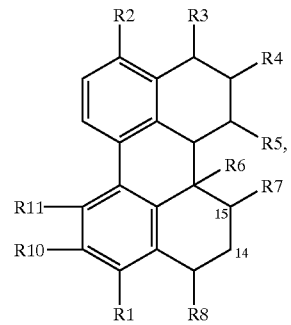

including all stereoisomeric forms of said compound of formula I, mixtures of said forms and compounds in any ratio, and/physiologically tolerated salts thereof, wherein:
R1, R2, R3, R4, R5, R6, R7, R8, R10 and R11 are independently selected from the group consisting of hydrogen;
($C_1$–$C_6$)-alkyl, in which alkyl is a straight or branched chain and is unsubstituted or substituted by one, two or three substituents independently selected from the group consisting of:
—OH; =O; —O—($C_1$–$C_6$)-alkyl, in which alkyl is a straight or branched chain and is unsubstituted or substituted by one, two or three substituents independently selected from the group consisting of:
—CN; —NH$_2$; =N—OH and =N—O—($C_1$–$C_6$)-alkyl, in which alkyl is a straight or branched chain;
—O—($C_2$–$C_6$)-alkenyl, in which alkenyl is a straight or branched chain and is unsubstituted or substituted by one, two or three substituents independently selected from the group consisting of:
—CN; —NH$_2$; =N—OH and =N—O—($C_1$–$C_6$)-alkyl, in which alkyl is a straight or branched chain; —O—($C_2$–$C_6$)-alkynyl, in which alkynyl is a straight or branched chain and is unsubstituted or substituted by one, two or three substituents independently selected from the group consisting of:
—CN; —NH$_2$; =N—OH and =N—O—($C_1$–$C_6$)-alkyl, in which alkyl is a straight or branched chain; -aryl, in which aryl is unsubstituted or substituted by one, two or three substituents independently selected from the group consisting of: halogen; —($C_1$–$C_4$)-alkyl, in which alkyl is a straight or branched chain; —O—($C_1$–$C_6$)-alkyl, in which alkyl is a straight or branched chain; —OH and —($C_1$–$C_4$)-alkyl, in which alkyl is a straight or branched chain and is substituted by one, two or three substituents selected from the group consisting of halogen;
—C(O)—OH; —C(O)—O—NH$_2$; —C(O)—O—($C_1$–$C_4$)-alkyl, in which alkyl is a straight or branched chain; —NH—($C_1$–$C_6$)-alkyl, in which alkyl is a straight or branched chain and is unsubstituted or substituted by one, two or three substituents independently selected from the group consisting of: —CN; —NH$_2$; =N—OH and =N—O—($C_1$–$C_6$)-alkyl, in which alkyl is a straight or branched chain; —NH—($C_2$–$C_6$)-alkenyl, in which alkenyl is a straight or branched chain and is unsubstituted or substituted by one, two or three substituents independently selected from the group consisting of: —CN; —NH$_2$;

=N—OH and =N—O—($C_1$-$C_6$)-alkyl, in which alkyl is a straight or branched chain; —NH—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —$NH_2$ and halogen;

($C_2$-$C_6$)-alkenyl, in which alkenyl is a straight or branched chain and is unsubstituted or substituted by one, two or three substituents independently selected from the group consisting of:

—OH; =O; —O—($C_1$-$C_6$)-alkyl, in which alkyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; -aryl, in which aryl is unsubstituted or substituted by one, two or three substituents independently selected from the group consisting of: halogen; —($C_1$-$C_4$)-alkyl, in which alkyl is a straight or branched chain; —O—($C_1$-$C_6$)-alkyl, in which alkyl is a straight or branched chain; —OH and —($C_1$-$C_4$)-alkyl, in which alkyl is a straight or branched chain and is substituted one, two or three times by halogen; —C(O)—OH; —C(O)—O—$NH_2$; —C(O)—O—($C_1$-$C_4$)-alkyl, in which alkyl is a straight or branched chain; —NH—($C_1$-$C_6$)-alkyl, in which alkyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —NH—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —NH—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —$NH_2$ and halogen;

($C_2$-$C_6$)-alkynyl, in which alkynyl is a straight or branched chain and is unsubstituted or substituted by one, two or three substituents independently selected from the group consisting of:

—OH; =O; —O—($C_1$-$C_6$)-alkyl, in which alkyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; -aryl, in which aryl is unsubstituted or substituted by one, two or three substituents independently selected from the group consisting of: halogen; —($C_1$-$C_4$)-alkyl, in which alkyl is a straight or branched chain; —O—($C_1$-$C_6$)-alkyl, in which alkyl is a straight or branched chain; —OH and —($C_1$-$C_4$)-alkyl, in which alkyl is a straight or branched chain and is substituted one, two or three times by halogen; —C(O)—OH; —C(O)—O—$NH_2$; —C(O)—O—($C_1$-$C_4$)-alkyl, in which alkyl is a straight or branched chain; —NH—($C_1$-$C_6$)-alkyl, in which alkyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —NH—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —NH—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —$NH_2$ and halogen;

—O—$R^9$, in which $R^9$ is selected from the group consisting of: ($C_1$-$C_6$)-alkyl, in which alkyl is a straight or branched chain and is unsubstituted or substituted by one, two or three substituents independently selected from the group consisting of: —OH; =O; —O—($C_1$-$C_6$)-alkyl, in which alkyl is a straight or branched chain and is unsubstituted or substituted by one, two or three substituents independently selected from the group consisting of: —CN; —$NH_2$; =N—OH; and =N—O—($C_1$-$C_6$)-alkyl, in which alkyl is a straight or branched chain; —O—($C_2$-$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; —O—($C_2$-$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$-$C_6$)-alkyl, in which alkyl is a straight or branched chain; -aryl, in which aryl is unsubstituted or substituted by one, two or three substituents independently selected from the group consisting of: halogen; —($C_1$–$C_4$)-alkyl, in which alkyl is a straight or branched chain; —O—($C_1$–$C_6$)-alkyl, in which alkyl is a straight or branched chain; —OH and —($C_1$–$C_4$)-alkyl, in which alkyl is a straight or branched chain and is substituted one, two or three times by halogen; —C(O)—OH; —C(O)—O—$NH_2$; —C(O)—O—($C_1$–$C_4$)-alkyl, in which alkyl is a straight or branched chain; —NH—($C_1$–$C_6$)-alkyl, in which alkyl is a straight or branched chain and is unsubstituted or substituted by one, two or three substituents independently selected from the group consisting of: —CN; —$NH_2$; =N—OH; and =N—O—($C_1$–$C_6$)-alkyl, in which alkyl is a straight or branched chain; —NH—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —$NH_2$ and halogen;

($C_2$–$C_6$)-alkenyl, in which alkenyl is a straight or branched chain and is unsubstituted or substituted by one, two or three substituents independently selected from the group consisting of: —OH; =O; —O—($C_1$–$C_6$)-alkyl, in which alkyl is a straight or branched chain and is unsubstituted or substituted by one, two or three substituents independently selected from the group consisting of: —CN; —$NH_2$; =N—OH; and =N—O—($C_1$–$C_6$)-alkyl, in which alkyl is a straight or branched chain; —O—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —O—($C_2$–$C_6$)-alkynyl, in which alkynyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; -aryl, in which aryl is unsubstituted or substituted by one, two or three substituents independently selected from the group consisting of: halogen; —($C_1$–$C_4$)-alkyl, in which alkyl is a straight or branched chain; —O—($C_1$–$C_6$)-alkyl, in which alkyl is a straight or branched chain; —OH and —($C_1$–$C_4$)-alkyl, in which alkyl is a straight or branched chain and is substituted one, two or three times by halogen; —C(O)—OH; —C(O)—O—$NH_2$; —C(O)—O—($C_1$–$C_4$)-alkyl, in which alkyl is a straight or branched chain; —NH—($C_1$–$C_6$)-alkyl, in which alkyl is a straight or branched chain and is unsubstituted or substituted by one, two or three substituents independently selected from the group consisting of: —CN; —$NH_2$; =N—OH; and =N—O—($C_1$–$C_6$)-alkyl, in which alkyl is a straight or branched chain; —NH—($C_2$–$C_6$)-alkenyl, in which alkenyl is a straight or branched chain and is unsubstituted or substituted by one, two or three substituents independently selected from the group consisting of: —CN; —$NH_2$; =N—OH and =N—O—($C_1$–$C_6$)-alkyl, in which alkyl is a straight or branched chain; —NH—($C_2$–$C_6$)-alkynyl, in which alkynyl is a straight or branched chain and is unsubstituted or substituted by one, two or three substituents independently selected from the group consisting of: —CN; —NH$_2$; =N—OH and =N—O—(C$_1$–C$_6$)-alkyl, in which alkyl is a straight or branched chain; —NH$_2$ and halogen;
—NH—R$^9$, in which R$^9$ is as defined above;
—NH—C(O)—H;
—NH—C(O)—R$^9$, in which R$^9$ is as defined above;
—NH-aryl, in which aryl is unsubstituted or independently substituted one, two or three times by R$^9$, in which R$^9$ is as defined above:
=N—OH;
=N—O—R$^9$, in which R$^9$ is as defined above;
—S—H;
—S—R$^9$, in which R$^9$ is as defined above;
—S(O)—R$^9$, in which R$^9$ is as defined above;
—S(O)$_2$—R$^9$, in which R$^9$ is as defined above; and
—SO$_2$, with the following further alternatives to the foregoing definition:
a) either R4 and R5 or R10 and R11, together with the carbon atoms to which they are, respectively, bonded, may form a 3-, 4-, 5- or 6-membered heteroalkyl or heteroaryl ring system which contains one or two heteroatoms selected from the group consisting of oxygen, nitrogen and sulfur; and
b) the bond between the ring carbons indicated as —C$_{14}$–C$_{15}$— in formula I may be either a single bond or a double bond; and the further proviso that:
c) R7 is not hydrogen.

2. A compound of the formula I as claimed in claim 1, wherein
a) each of R1, R2, R3 and R6 is —OH,
b) R4 and R5, together with the carbon atoms to which they are bonded, form an epoxide,
c) R7 is the radical —S—CH$_2$—CHOH—COOH,
d) R8 is =O,
e) each of R10 and R11 is hydrogen atom; and
f) the bond between the ring carbons designated as —C$_{14}$–C$_{15}$— is a single bond, and/or physiologically tolerated salts thereof of the compound of the formula I.

3. A compound as claimed in claim 2, which has the structure of formula II

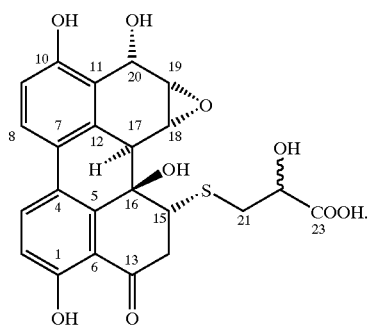

4. A process for preparing a compound of formula I as claimed in claim 1, which comprises
a) culturing the microorganism DSM 14452, or a mutant or variant thereof, in an aqueous nutrient medium;
b) isolating from the culture medium of step a) the compound thioperylenol;
c) purifying the thiophenyl thus obtained;
d) converting thioperylenol, whether or not obtained by the foregoing steps, by means of chemical derivatization, into a compound of the formula I;

e) if necessary, i) resolving the compound of the formula I so obtained, which, because of its chemical structure, appears in enantiomeric forms, into its pure enantiomers either by forming salts with enantiomerically pure acids or bases, or by chromatography on chiral stationary phases or by derivatizing with chiral, enantiomerically pure compounds, such as amino acids, ii) separating the diastereomers which are thus obtained and iii) eliminating the chiral auxiliary groups; and f) optionally, either isolating the compound of the formula I which has been thus prepared in free form or, when acidic or basic groups are present, converting it into a physiologically tolerated salts.

5. A pharmaceutical composition which contains a therapeutically effective amount of at least one compound as claimed in claim 1, together with a pharmaceutically suitable and physiologically tolerated carrier substance or additive and/or other active compounds and auxiliary substances.

6. A method of treating or preventing diseases in which high blood platelet aggregations occur, comprising administering to a mammal in need thereof an effective amount of a compound of claim 1 in pharmaceutically acceptable form.

7. The method of claim 6 wherein said compound is as defined in claim 2.

8. The method of claim 6, wherein said compound is selected from the group consisting of:
thioperylenol, a compound of formula I, in which: R1, R2, R3 and R6 are, in each case, —OH; R4 and R5, together with the carbon atoms to which they are in each case bonded, form an epoxide; R7 is the radical —S—CH$_2$—CHOH—COOH; R8 is =O; R10 and R11 are, in each case, hydrogen; and the bond between —C$_{14}$–C$_{15}$— is a single bond;
alterperylenol, a compound of formula I, in which R1, R2, R5 and R6 are, in each case, —OH; R3 and R8 are, in each case, =O; R4, R7, R10 and R11 are, in each case, hydrogen; and the bond between —C$_{14}$–C$_{15}$— is a double bond;
altertoxin I, a compound of formula I in which R1, R2, R5 and R6 are, in each case, —OH; R3 and R8 are, in each case, =O; R4, R7, R10 and R11 are, in each case, hydrogen; and the bond between —C$_{14}$–C$_{15}$— is a single bond;
altertoxin II, a compound of formula I, in which R1, R2 and R6 are, in each case, —OH; R3 and R8 are in each case =O; R4 and R5, together with the carbon atoms to which they are in each case bonded, form an epoxide; R7, R10 and R11 are, in each case, hydrogen; and the bond between —C$_{14}$–C$_{15}$— is a single bond; and
altertoxin III, a compound of formula I, in which R1 and R3 are, in each case, =O, R2 and R8 are, in each case, —OH; R4 and R5 and R10 and R11, together with the carbon atoms to which they are in each case bonded, form an epoxide; R6 and R7 are, in each case, hydrogen; and the bond between —C$_{14}$–C$_{15}$— is a single bond.

9. The method of claim 6, wherein said disease in which high blood platelet aggregations occur is selected from the group consisting of myocardial infarction, unstable angina pectoris, stroke, transitory ischemic attacks and peripheral arterial occlusion diseases such as intermittent claudication.

* * * * *